United States Patent [19]

Weeks

[11] Plant 4,713

[45] May 12, 1981

[54] ROSE PLANT

[76] Inventor: O. L. Weeks, 4759 Philadelphia St., Chino, Calif. 91710

[21] Appl. No.: 139,837

[22] Filed: Apr. 14, 1980

[51] Int. Cl.[3] ..... A01H 5/00

[52] U.S. Cl. ..... Plt./26

[58] Field of Search ..... Plt./26

*Primary Examiner*—Robert E. Bagwill

*Attorney, Agent, or Firm*—Vincent G. Gioia

[57] ABSTRACT

A new floribunda rose variety of soft pink flowers borne in medium sized clusters which lighten upon aging.

1 Drawing Figure

1

The present invention relates to a new and distinct variety of rose plant of the floribunda rose class, which was originated by my crossing as seed parent the rose known as "Plain Talk" and the rose known as "Angel Face" as pollen parent.

Among the novel characteristics possessed by this new variety which distinguish it from its parents and all other varieties of which I am aware are soft pink flowers borne in medium clusters developing from high centered buds and a vigorous, free branching plant with abundant foliage. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine floribunda rose with medium clusters of blooms displayed on a vigorous, bushy, free branching plant with abundant foliage. Plants are very floriferous and often covered with flowers. Although the soft pink color lightens upon aging flowers remain attractive and the plant as a whole displays different pink tones due to presence of flowers of different maturity.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "48B" is plate 48B of the Royal Horticultural Society Color Chart.

Parentage: Seedling.

*Seed parent.*—"Plain Talk".

*Pollen parent.*—"Angel Face".

Class: Floribunda.

The following observations are made of specimens grown outdoors in San Bernardino County, Calif. during the month of October.

1. FLOWER

Blooming habit: Intermittent to continuous.

A. Bud:

2

(1) *Size.*—Small.

(2) *Form.*—Short, ovoid, slender, foliated until sepals divide.

(3) *Color.*—When sepals first divide, bud color shows pink and yellow tones with yellow predominant at point of attachment and pink at petal edge portion. The yellow tone is 19B, 19C and 19D. The pink coloring seen best at apex and along bud petal edge section is 48B to 48D.

(4) *Sepals.*—Simple, fall quickly, about same length as bud, recurve.

(5) *Peduncle.*—Length — short, some hairs. Aspect — straight and curved. Strength — strong. Color — 137 B or C.

B. Bloom:

(1) *Size.*—Average size when fully expanded — about 2½-inches to 3-inches.

(2) *Borne.*—Clusters of 2 to 5 blooms.

(3) *Form.*—Ovoid at first, flowers open fast, petals roll outward loosely.

(4) *Petalage.*—Number of petals under normal conditions — about 24 to 28.

(5) *Color.*—As petals unfurl predominant color is 50C which is the color of the underside of the petals. The top surface of petals are 50D and this color predominates as flowers open when more top surfaces of more petals are seen. Fresh open blooms display yellow coloring of stamens and pollen which darken upon aging. Petals of mature blooms lighten still further to 49D.

C. Petals:

(1) *Texture.*—Thin, soft.

(2) *Appearance.*—Satiny.

(3) *Form.*—Outside round.

(4) *Arrangement.*—Regularly arranged.

(5) *Petaloids in center.*—Ordinary.

(6) *Persistence.*—Drop off cleanly.

(7) *Fragrance.*—Moderate.

(8) *Lasting quality.*—Long lasting on plant and as cut flower (3 to 5 days).

2. REPRODUCTIVE ORGANS

A. Stamens, filaments and anthers:

(1) *Arrangement.*—Many stamens regularly arranged around few pistils, mixed with petaloids.

(2) *Color.*—Yellow.

B. Pollen: Color — yellow.

C. Styles: Uneven, short, thin, bunched.

D. Stigmas: Color — tan.

E. Hips: None observed.

3. PLANT

A. Form: Upright, bushy.

B. Growth: Vigorous, free branching.

C. Foliage: Compound 3 to 5 leaflets.

(1) *Size.*—Small to medium.

(2) *Quantity.*—Abundant.

(3) *Color.*—New foliage: very young is reddish-gray 180A maturing to: Upper side — near to 147B. Under side — near to 189A. Old foliage: Upper side — near to 139A. Under side — near to 189A.

(4) *Shape.*—Ovoid, cuspidate.

(5) *Texture.*—Thin.

(6) *Edge.*—Coarsely serrated.

(7) *Serration.*—Simple.

(8) *Leaf stem.*—Color — near to 146B.

(9) *Stipules.*—Medium.

(10) *Resistance to disease.*—Blackspot — good. Rust — good.

D. Wood:

(1) *New wood.*—Color — near 191A to 137B. Bark — smooth, shiny.

(2) *Old wood.*—Color — near 189A. Bark — smooth, shiny.

E. Thorns:

(1) *Thorns.*—Quantity (main stalk): few. Form — slightly downward. Length — medium. Color — tan. Position — scattered.

(2) *Prickles.*—Few to none.

F. Winter hardiness: Good winter hardiness.

I claim:

1. A new and distinct variety of rose plant of the floribunda class, substantially as shown and described, characterized particularly by clusters of soft pink colored flowers which lighten upon aging beginning with buds showing yellow coloring at petal point of attachment and pink at petal edge and opening to soft pink blooms showing golden yellow centers in freshly open flowers.

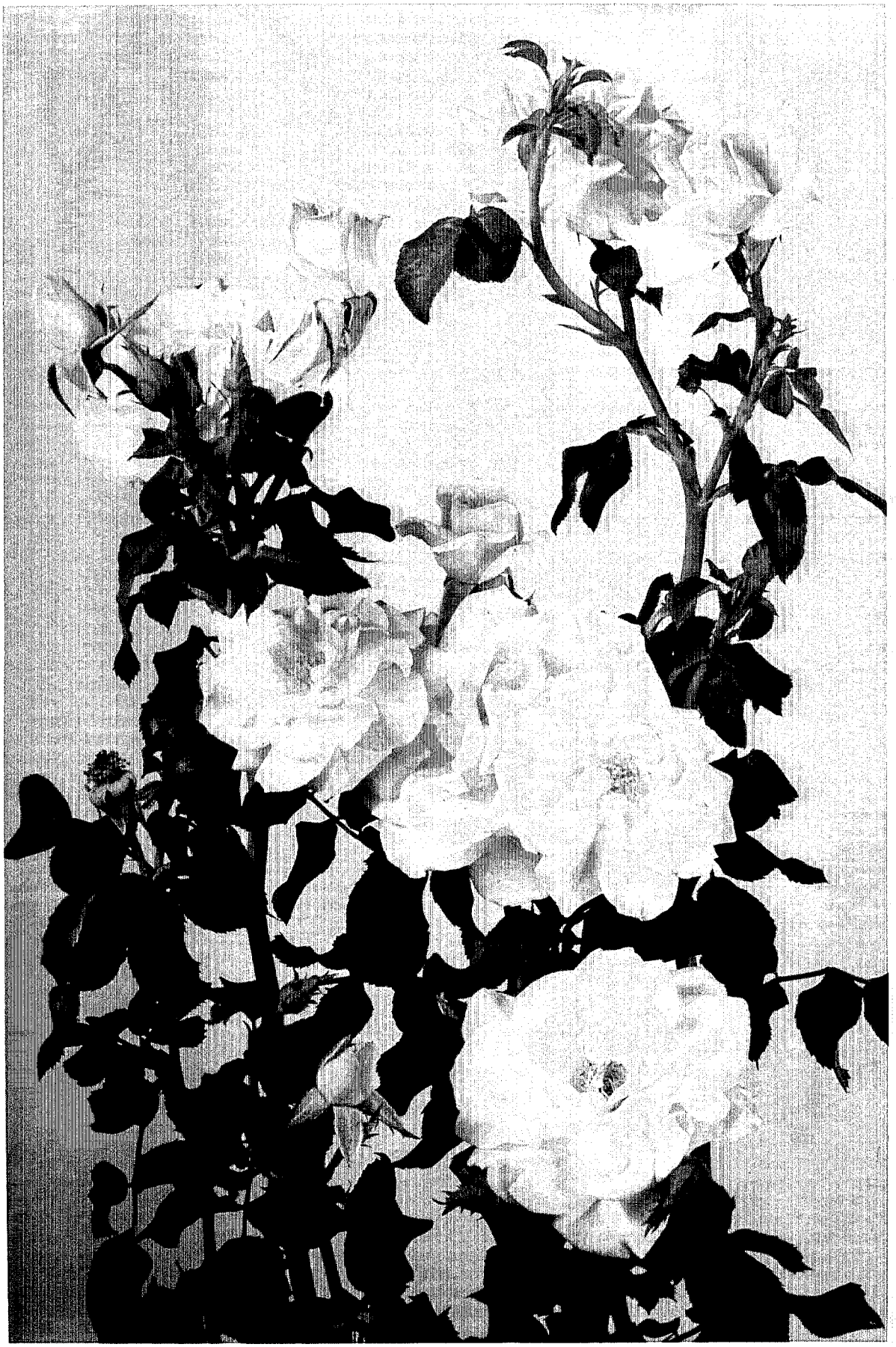

* * * * *